United States Patent [19]

Schaffner et al.

[11] B 4,001,335

[45] Jan. 4, 1977

[54] PRODUCTION OF 3-MONOCHLORO-2,4,5-TRIALKYLBENZOPHENONES AND 3,6-DICHLORO-2,4,5-TRIALKYLBENZOPHENONES

[75] Inventors: Ernst Schaffner, Ludwigshafen; Heinz Eilingsfeld, Frankenthal; Ernst Schefczik; Manfred Patsch, both of Ludwigshafen, all of Germany

[73] Assignee: BASF Aktiengesellschaft, Ludwigshafen (Rhine), Germany

[22] Filed: Nov. 15, 1973

[21] Appl. No.: 416,257

[44] Published under the second Trial Voluntary Protest Program on March 16, 1976 as document No. B 416,257.

[30] Foreign Application Priority Data

Nov. 18, 1972 Germany .......................... 2256662

[52] U.S. Cl. ............................... 260/591; 260/369; 260/377; 260/515 A; 260/524 R
[51] Int. Cl.$^2$ .......................................... C07C 49/80
[58] Field of Search ................................... 260/591

[56] References Cited

UNITED STATES PATENTS 2,012,301  8/1935  Clark et al. ......................... 260/591

OTHER PUBLICATIONS

Dokunikhin et al., Chem. Abstracts, 66, 104844g (1967).

*Primary Examiner*—D. Horwitz
*Attorney, Agent, or Firm*—Johnston, Keil, Thompson & Shurtleff

[57] ABSTRACT

The production of 3-monochloro and 3,6-dichloro derivatives of 2,4,5-trialkylbenzophenones by reaction of 2,4,5-trialkylbenzophenones with chlorine, and the new 3-monochloro-2,4,5-trialkylbenzophenones and 3,6-dichloro-2,4,5-trialkylbenzophenones themselves. The products are starting materials for the production of dyes and pesticides.

8 Claims, No Drawings

PRODUCTION OF 3-MONOCHLORO-2,4,5-TRIALKYLBENZOPHE-NONES AND 3,6-DICHLORO-2,4,5-TRIALKYLBENZOPHE-NONES

The invention relates to a process for the production of 3-monochloro-2,4,5-trialkylbenzophenones and 3,6-dichloro-2,4,5-trialkylbenzophenones by the reaction of 2,4,5-trialkylbenzophenones with chlorine.

Many method for halogenating benzene derivatives in the nucleus are known from Houben-Weyl, "Methoden der organischen Chemie", volume V/3, pages 12 et seq., pages 511 et seq., and volume V/4, pages 13 et seq. and 517 et seq. In the case of systems having two phenyl nuclei which are connected together direct or by way of alkylene radicals the halogenation has not been described or it gives conflicting results, for example a halogenation of the alkyl radical, mixtures of differently halogenated components or changes in the basic substance. Thus in Rodd, "Chemistry of Carbon Compounds", (Elsevier, N.Y. 1956, volume IIIb, pages 1055 to 1063, it is recommended that nuclear-halogenated diphenylmethanes and benzophenones should not be prepared by direct halogenation but by other methods. When diphenylmethane is heated with phosphorus pentachloride it gives benzyl trichloride and benzophenone dichloride (Rodd, loc. cit., page 1058); the combination of the halogen is described as labile. Direct chlorination or bromination of diphenyl gives 4-, 4,4'-, 2- and 2,4'-halogen derivatives. Chlorination of 1,1,1-trichloro-2,2-bis-p-chlorophenylethane in carbon tetrachloride in the presence of phosphorus trichloride in sunlight (Rodd, loc. cit., page 1119) gives the 1,1,1,2-tetrachloroc compound. The solvent may also play an important role: thus bromination of 1,2-diphenylethane in a solvent which does not contain any hydroxyl groups, for example carbon tetrachloride, gives the 1,2-dibromo compound; reaction in glacial acetic acid given a mixture of 1,2,p,p,'- and 1,2,0,p'-tetrabromo-1,2-diphenylethanes (Rodd, loc.cit., page 1136). Chloroalkyl groups may be eliminated in the nuclear chlorination; thus for example 3,4-dichlorobenzotrichloride is formed from 2-chloro-1,4-bistrichloromethylbenzene (Houben-Weyl, loc. cit., volume V/3, page 666). In the chlorination of o-methylbiphenyl and o-methylbenzophenone systems cyclization may occur, for example to form tetrachlorofluorenacene compounds or dichloroanthrone compounds.

According to the teaching of Rodd (loc. cit., page 1065) halogenated benzophenones are always prepared by oxidation of diphenylmethanes or benzhydrols or by Friedel-Crafts syntheses of benzoyl halides with appropriately halogenated benzenes. An article in Bullet Soc.Chim. Fr., volume 51 (1932), pages 653 et seq. discloses that chlorination by an electrochemical method is easier than chlorination with elementary chlorine; in the case of benzophenone only a viscous inseparable chlorination mixture is obtained as the end porduct.

Chlorination of a benzophenone bearing three alkyl groups as substituents in a phenyl nucleus has not hitherto been described.

It is an object of this invention to provide a new process for the selective production of 3-monochloro and 3,6-dichloro derivatives of 2,4,5-trialkylbenzophenones in a simple manner and in good yields and purity.

Another object of this invention is new 3-monochloro-2,4,5-trialkylbenzophenones and new 3,6-dichloro-2,4,5-trialkylbenzophenones.

Yet another object of this invention is 3,6-dichloro-2,4,5-trimethylbenzophenone.

We have found that 3-monochloro-2,4,5-trialkylbenzophenones and 3,6-dichloro-2,4,5-trialkylbenzophenones of the formula (I):

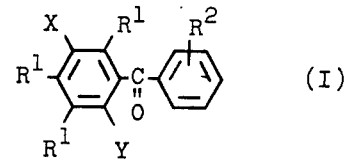

in which the individual radicals $R^1$ may be identical or different and each is alkyl, $R^2$ is hydrogen or halogen, Z is chloro and Y is hydrogen or chloro are X advantageously by reacting a 2,4,5-trialkylbenzophenone of the formula (II):

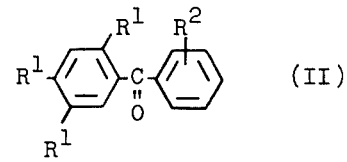

in which $R^1$ and $R^2$ have the above meanings with chlorine in the presence of iodine and/or an iron compound.

In the case when 2,4,5-trimethylbenzophenone is used, the reaction may be represented by the following equation:

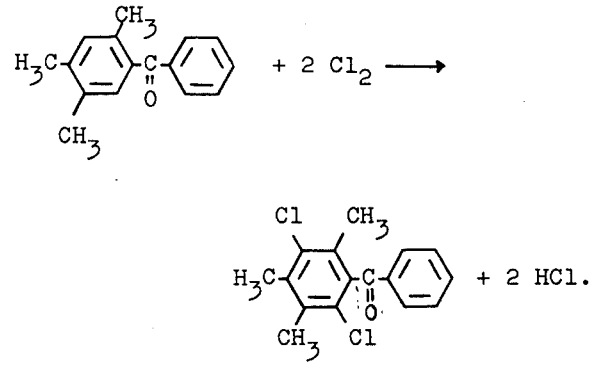

Having regard to the prior art the process of the invention gives 3-monochloro and 3,6-dichloro derivatives of 2,4,5-trialkylbenzophenones selectively in a simple manner, in good yields and high purity. Formation of numerous isomeric monochloro, dichloro, trichloro and higher polychloro compounds which bear chloro as substituent on both nuclei or chlorination of the alkyl groups which are substituents on the nucleus are not observed to any significant extent. Similarly secondary reactions such as elimination of alkyl groups, cyclization, or fission of the starting material for example into benzene or benzoyl compounds does not play any significant role. A large number of both polar and nonpolar solvents may be used. None of these advantageous results was to have been expected having regard to the prior art.

The 2,4,5-trialkylbenzophenones used as starting materials (II) may be synthesized by the Friedel-Crafts method from optionally halogenated benzoyl chloride and 1,3,4-trialkylbenzenes. Preferred starting materials (II) and accordingly preferred end products (I) are those in whose formulae the individual radicals $R^1$ are identical or different and each is alkyl of one to seven and preferably from one to four carbon atoms, particularly methyl, $R^2$ is hydrogen, chloro or bromo, X is chloro and Y is hydrogen or chloro. The alkyl radicals may be linear or branched.

Examples of suitable starting materials (II) are: 2,4,5-trimethylbenzophenone, 2,4,5-triethylbenzophenone, 2,4,5-triisopropylbenzophenone, 2,4,5-n-propylbenzophenone, 2-methyl-4,5-diethylbenzophenone, 2,4-dimethyl-5-ethylbenzophenone and the said compounds which bear a chlorine atom or a bromine atom as substituent in the second phenyl nucleus in the ortho-position, meta-position or para-position to the carbonyl group.

The reaction is generally carried out continuously or batchwise at a temperature of from −10° to 140°C, conveniently at from −5° to 50°C in the case of the production of 3-monochloro-2,4,5-trialkylbenzophenones and at from 80° to 120°C in the case of the production of 3,6-dichlorocompounds, at atmospheric or superatmospheric pressure. Solvents which are inert under the reaction conditions are used as a rule to dissolve or suspend the starting material or reaction mixture. Organic solvents having a boiling point at standard pressure or at a pressure up to 10 atmospheres of more than 100°C and preferably of from 100° to 190°C are advantageously suitable. The following are suitable as solvents for example: halohydrocarbons, particularly chlorohydrocarbons, for example tetrachloroethylene, tetrachloroethane, carbon tetrachloride, chloroform, trichloroethylene, pentachloroethane, cis-dichloroethylene, 1,2-dichloroethane, methylene chloride, 1,1-dichloroethane, 1,2-cis-dichloroethylene; nitrohydrocarbons such as nitromethane, nitroethane, nitrobenzene, o-chloronitrobenzene, m-chloronitrobenzene, p-chloronitrobenzene or o-nitrotoluene; nitriles such as acetonitrile, benzonitrile or m-chlorobenzonitrile; aliphatic and cycloaliphatic hydrocarbons such as hexane, heptane, nonane, α-pinene, pinane, o-cymene, m-cymene, p-cymene, gasoline fractions within the said boiling point range, cyclohexane, methylcyclohexane, petroleum ether, decahydronaphthalene, ligroin, 2,2,4-trimethylpentane, 2,2,3-trimethylpentane, 2,3,3-trimethylpentane, octane; preferably organic acids, for example acetic acid, propionic acid, chloroacetic acid, oxalic acid, formic acid, adipic acid, bromoacetic acid, and iodoacetic acid; and appropriate mixtures of these. The solvent is conveniently used in an amount of from 50 to 1,000% by weight and preferably from 500 to 1,000% by weight based on starting material (II).

The reaction is carried out in the presence of iodine, and optionally also substances yielding iodine under the reaction conditions such as iodine(I) chloride, or of iron compounds, conveniently the iron salts or organic or inorganic acids, as chlorination catalysts. Substances which form iron(III) chloride under the reaction conditions, such as metallic iron, for example iron powder, iron turnings, or $Fe_2O_3$. Examples of suitable salts of iron are: iron sulfate, phosphate, nitrate, perchlorate, toluenesulfonate, benzenesulfonate, borate, borofluoride, acetate, formate, propionate, oxalate, adipate, benzoate, phthalate, glycolate, tartrate and preferably iron(III) chloride. The elementary chlorine is generally used in the case of the production of the monochlorocompound in an amount of 1 to 3 and preferably 1.5 to 2.5 moles and in the case of the production of the dichloro compound in an amount of 3 to 8 and advantageously 4 to 7 moles per mole of starting material (II). The halogenation catalyst is used in the case of the production of the monochloro compound in an amount of from 0.10 to 1% and preferably from 0.05 to 0.2% by weight and in the case of the production of the dichloro compound in an amount of from 0.1 to 10% and advantageously from 0.5 to 1.5% by weight based on starting material (II).

The reaction may be carried out as follows: a mixture of starting material (II), catalyst and if desired a solvent is kept at the reaction temperature for from thirty minutes to eight hours. The end product is then separated from the reaction mixture by a conventional method, for example by distillation.

When it is desired to prepare a 3-monochloro-2,4,5-trialkylbenzophenone the abovementioned temperature range and amounts of chlorine and catalyst are chosen. When the temperature and/or the amount of chlorine and catalyst are increased, the dichloro compound is formed to an increasing extent.

New compounds which can be prepared by the process of the invention are valuable starting materials for the production of dyes and pesticides. Thus by oxidation with air in the presence of suitable catalysts, they may be oxidized into tricarboxylic acids and cyclized with sulfuric acid into anthraquinone derivatives which are starting materials for disperse dyes for polyesters which are fast to wet treatments, laundering and light. For example in the said manner 3,6-dichloro-2,4,5-trimethylbenzophenone is converted into anthraquinone-1,4-dichloro-2,3-dicarboxylic anhydride which by reaction with a primary alkylamine and replacement of the two chlorine atoms by amino groups gives the brilliant blue 1,4-diaminoanthraquinone-2,3-dicarboxylic acid N-alkylimide dyes.

The following Examples illustrate the invention. The parts specified are by weight.

EXAMPLE 1

200 parts of chlorine is passed over 3½ hours at 70° to 80°C into a solution of 158 parts of 2,4,5-trimethylbenzophenone and 0.25 part of iodine in 600 parts of glacial acetic acid. The reaction mixture is distilled at subatmospheric pressure. 189.5 parts (86.6% of theory) of 2,4,5-trimethyl-3,6-dichlorobenzophenone is obtained at 168° to 175°C at 0.05 mmHg. After recrystallization from methanol it has a melting point of 105° to 107°C.

EXAMPLE 2

100 parts of 2,4,5-trimethylbenzophenone is dissolved in 500 parts of glacial acetic acid and then 5 parts of iron(III) chloride is added. 100 parts of chlorine is passed into the solution at 80° to 85°C over 5 hours. The mixture is then worked up by distillation analogously to Example 1. 106 parts (81.5% of theory) of 2,4,5-trimethyl-3,6-dichlorobenzophenone is obtained having a melting point of 105° to 107°C after having been recrystallized from methanol.

EXAMPLE 3

5 parts of iron(III) oxide is added to 50 parts of 2,4,5-trimethylbenzophenone in 300 parts of glacial acetic acid. Chlorination is then carried out by passing 50 parts of chlorine in over a period of 3 hours at 80° to 85°C. The mixture is distilled as described in Example 1. 52.5 parts (80.5% of theory) of 2,4,5-trimethyl-3,6-dichlorobenzophenone is obtained. After it has been recrystallized from methanol it has a melting point of 105° to 107°C.

EXAMPLE 4

33.6 parts of 2,4,5-trimethylbenzophenone and 0.1 part of iodine are dissolved in 150 parts of trichloroethylene. 19.2 parts of chlorine is passed into this solution at 0° to 5°C over a period of 3 hours. The mixture is stirred for another 5 hours at ambient temperature and then distilled at subatmospheric pressure. 26 parts (67.2% of theory) of 3-chloro-2,4,5-trimethylbenzophenone is obtained at 155° to 165°C at 0.1 mmHg.

We claim:

1. A 3,6-dichloro-2,4,5-trialkylbenzophenone of the formula

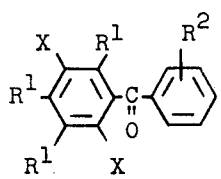

in which the individual radicals $R^1$ may be identical or different and each is alkyl, $R^2$ is hydrogen or halogen and X is chloro.

2. A 3-monochloro-2,4,5-trialkylbenzophenone of the formula:

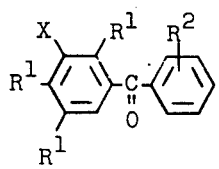

in which the individual radicals $R^1$ may be identical or different and each is alkyl, $R^2$ is hydrogen or halogen and X is chloro.

3. 3,6-dichloro-2,4,5-trimethylbenzophenone.

4. The compound claimed in claim 1 of the formula

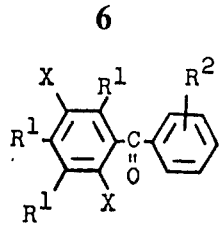

in which the individual radicals $R^1$ may be identical or different and each is alkyl of one to seven carbon atoms, $R^2$ is hydrogen, chloro or bromo and X is chloro.

5. The compound claimed in claim 1 of the formula

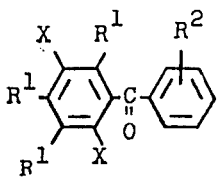

in which the individual radicals $R^1$ may be identical or different and each is alkyl of one to four carbon atoms, $R^2$ is hydrogen, chloro or bromo and X is chloro.

6. The compound claimed in claim 2 of the formula

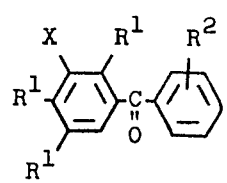

in which the individual radicals $R^1$ may be identical or different and each is alkyl of one to seven carbon atoms, $R^2$ is hydrogen, chloro or bromo and X is chloro.

7. The compound claimed in claim 2 of the formula

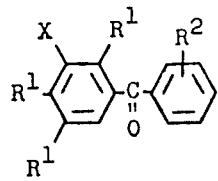

in which the individual radicals $R^1$ may be identical or different and each is alkyl of one to four carbon atoms, $R^2$ is hydrogen, chloro or bromo and X is chloro.

8. 3-chloro-2,4,5-trimethylbenzophenone.

* * * * *